United States Patent
Hainzl et al.

(10) Patent No.: US 9,924,864 B2
(45) Date of Patent: Mar. 27, 2018

(54) EYE-TRACKER ILLUMINATION

(75) Inventors: Richard Hainzl, Sollentuna (SE); Mattias Kuldkepp, Sollentuna (SE); Peter Blixt, Hägersten (SE); Mårten Skogö, Danderyd (SE)

(73) Assignee: Tobii AB, Danderyd (SE)

( * ) Notice: Subject to any disclaimer, the term of this patent is extended or adjusted under 35 U.S.C. 154(b) by 364 days.

(21) Appl. No.: 14/131,657

(22) PCT Filed: Jun. 14, 2012

(86) PCT No.: PCT/SE2012/050651
§ 371 (c)(1),
(2), (4) Date: Jun. 13, 2014

(87) PCT Pub. No.: WO2013/009235
PCT Pub. Date: Jan. 17, 2013

(65) Prior Publication Data
US 2014/0293226 A1    Oct. 2, 2014

Related U.S. Application Data

(60) Provisional application No. 61/505,977, filed on Jul. 8, 2011, provisional application No. 61/548,583, filed on Oct. 18, 2011.

(51) Int. Cl.
*A61B 3/14* (2006.01)
*A61B 3/113* (2006.01)
(Continued)

(52) U.S. Cl.
CPC .............. *A61B 3/113* (2013.01); *G02B 5/18* (2013.01); *G02B 27/0093* (2013.01); *G06F 3/013* (2013.01); *G06K 9/00604* (2013.01)

(58) Field of Classification Search
CPC .............................. A61B 3/113; G06F 3/013
(Continued)

(56) References Cited

U.S. PATENT DOCUMENTS

2004/0213463 A1   10/2004   Morrison
2006/0291020 A1   12/2006   Knox et al.
(Continued)

FOREIGN PATENT DOCUMENTS

DE   102005014640 A1   10/2006
WO         0152722 A1    7/2001
WO      2007015141 A2    2/2007

*Primary Examiner* — Jack Dinh
(74) *Attorney, Agent, or Firm* — Kilpatrick Townsend & Stockton LLP

(57) ABSTRACT

A subject (180) is illuminated whose movements of at least one eye are to be registered by an eye-tracker for producing resulting data ($D_{EYE}$). To this aim, a coherent light source in light producing means (140) produces at least one well-defined light beam (L1, L2). A diffractive optical element is arranged between the coherent light source and an output from the light producing means (140). The diffractive optical element is configured to direct a light beam (L1) towards at least a first designated area (A1) estimated to cover the at least one eye of the subject (180). Image registering means (150) registers light from the at least one light beam (L1, L2) having been reflected against the subject (180). The resulting data ($D_{EYE}$) are produced in response to these light reflections, which resulting data ($D_{EYE}$) represent movements of the at least one eye of the subject (180).

17 Claims, 2 Drawing Sheets

(51) Int. Cl.
*G02B 5/18* (2006.01)
*G06F 3/01* (2006.01)
*G02B 27/00* (2006.01)
*G06K 9/00* (2006.01)

(58) Field of Classification Search
USPC .................................................. 351/210, 209
See application file for complete search history.

(56) References Cited

U.S. PATENT DOCUMENTS

| | | |
|---|---|---|
| 2008/0204847 A1 | 8/2008 | Kamm et al. |
| 2008/0212034 A1 | 9/2008 | Aksyuk et al. |
| 2009/0174919 A1 | 7/2009 | Moss |
| 2009/0207467 A1 | 8/2009 | Meyers et al. |
| 2010/0066975 A1 | 3/2010 | Rehnstrom |
| 2011/0109880 A1 | 5/2011 | Nummela |
| 2012/0127573 A1 | 5/2012 | Robinson et al. |

EYE-TRACKER ILLUMINATION

CROSS REFERENCE TO RELATED APPLICATIONS

This application is a national stage entry of PCT/SE2012/050651, filed Jun. 14, 2012, which claims priority to U.S. Provisional Application No. 61/548,583, filed Oct. 18, 2011, and U.S. Provisional Application No. 61/505,977, filed Jul. 8, 2011. This application also claims priority to European Patent Application No. 11184628.3, filed Oct. 11, 2011. The entire disclosures of which are incorporated by reference herein for all purposes.

FIELD OF INVENTION

The present invention relates to illumination of a subject whose movements of at least one eye are to be registered by an eye-tracker to produce resulting data (i.e. information regarding eye and/or gaze positions). This data, in turn, may either be used to control a computer apparatus, or be registered exclusively for analysis purposes (e.g. in connection with psychology studies, or when diagnosing various medical conditions). Accurate information on the position of each eye of an observer is essential for an auto-stereoscopic display to ensure that the correct images are rendered and projected towards each eye in order to produce an immersive three dimensional effect. More particularly, the invention relates to an apparatus according to the preamble of claim 1.

THE BACKGROUND OF THE INVENTION AND PRIOR ART

The prior art includes directional optical illuminators for eye-trackers. Such illuminators are advantageous relative to static ditto because, at each point in time, they only illuminate a fraction of a surface inside a volume within which the subject moves. Thereby, power is conserved corresponding to the size of the non-illuminated surface that would otherwise have been illuminated. US 2010/0066975 describes a solution, using a matrix-based illuminator with imaging optics, or a collimated beam, and a tiltable mirror to direct illumination towards the user of an eye-tracker.

Furthermore, diffractive optical elements (DOEs) are known, which are configured to transform a coherent light beam into an arbitrary intensity pattern. A brief DOE description is available via the URL http://www.rpcphotonics.com/optical.asp.

US 2004/0213463 reveals a solution for imaging and range detection, wherein a DOE-based technique is used for spatial encoding of light. Here, the position and shape of a light pattern can be changed instantly by inserting a different DOE into the light beam.

DOEs are sometimes also referred to as holographic optical elements. In such cases, the DOE often includes a phase mask, analog or digital, which is configured to transform a coherent light beam into a desired spatial pattern. The phase amplitude is typically less than one wavelength. It is also possible that the DOE includes an amplitude mask.

PROBLEMS ASSOCIATED WITH THE PRIOR ART

Although the solution disclosed in US 2010/0066975 has many important qualities, there is room for improvements. For example, the design is based on classical optics, such as imaging lenses and mirrors. This, in turn, renders the design relatively bulky, complex and susceptible to mechanical damage.

In general, the traditional eye-tracker illuminators, which are based on LED and classical optics technology, are also associated with the following disadvantages.

The efficiency of an LED in terms of transferring electrical energy into light energy is relatively low. The efficiency in optics is likewise relatively low. Additionally, due to wide bandwidth, LED illuminators may unintentionally produce visible light although their peak wavelength is in the NIR spectrum. Of course, this may be distracting to the illuminated subject. Due to the wide bandwidth used, ambient light may also reach the image sensor, and thus cause disturbances.

When aiming for bright pupil eye tracking it is desirable that the illuminator be located as close as possible to the optical axis of the image registering means. A smallest possible illuminator is therefore attractive. The LED illuminators normally used in today's eye-trackers contain a matrix of multiple LEDs. Consequently, the LED illuminator becomes relatively large. Furthermore, the production cost scales as the number of chips needed. Since multiple LEDs correspond to multiple chips, the cost for an LED illuminator tends to be rather high.

Another characteristic of an LED is that it represents a so-called Lambertian light source. This means that its radiance is independent of direction. In other words, the radiation angle extends ±90 degrees, typically at ±60 degrees full width half maximum. Therefore, large numerical aperture optics is required for coupling efficiently, i.e. high transmission, which, in turn, renders the optics bulky and expensive.

SUMMARY OF THE INVENTION

The object of the invention is to mitigate the above problems and accomplish an uncomplicated, compact, robust and yet energy-efficient illumination solution for eye-tracker implementations.

According to the invention, the object is achieved by the initially described apparatus, wherein the light producing means includes a coherent light source and a diffractive optical element. The coherent light source is configured to generate coherent light of the well-defined light beam. Preferably the coherent light source contains a multi-mode laser diode showing some degree of coherence and having a bandwidth of less than 10 nm. However, also any other form of illuminator showing at least some degree of coherence may be used as the coherent light source. The diffractive optical element is configured to direct the light beam towards a first designated area that is estimated to cover at least one eye of the subject whose eye movements are to be registered. Preferably, the apparatus is configured to adaptively control a location of the first designated area, so that the first designated area covers an estimated eye region of the subject at each point in time.

This apparatus is advantageous because it enables precise illumination of the region being most relevant for the eye-tracking.

According to one preferred embodiment of the invention, the first designated area represents an illumination pattern, and the illuminated area is located within a field of view of the image registering means. Hence, a minimal amount of light is wasted, i.e. very little light is directed towards areas where it is not needed for image registering.

According to another preferred embodiment of the invention, the apparatus includes a speckle reduction means. The speckle reduction means is configured to reduce speckle-related intensity variations in the light from the coherent light source within the first designated area by causing the light from the coherent light source to be essentially evenly distributed over the first designated area during a predetermined interval of time, typically corresponding to the time required for an image registering means to capture image data based upon which the resulting data are produced.

Thus, the speckle reduction means may include an oscillator configured to cause the diffractive optical element to move relative to the coherent light source. Alternatively, the coherent light source may include a static multimode laser (transverse and/or longitudinal) configured to emit light with a spectrum containing at least two separate spectral lines, where the light represented by each of said at least two lines is associated with a particular speckle pattern. Hence, the resulting total light distribution over the first designated area becomes essentially even. As yet an alternative, the speckle reduction means may include a modulating means configured to time-modulate the coherent light source in such a manner that it produces light with a temporally varying speckle pattern. Again, over time, the resulting total light distribution over the first designated area becomes essentially even.

According to yet another preferred embodiment of the invention, the apparatus includes a light steering element configured to receive the coherent light and direct at least a fraction of the received light towards the subject. Preferably, the light steering element contains a diffractive optical element configured to direct received light as a part of the light beam towards the first designated area. Consequently, the apparatus attain a robust and compact design.

According to a further preferred embodiment of the invention, the image registering means includes a filter element arranged upstream of a sensor element configured to produce the resulting data. The filter element is configured to block visible light, so as to reduce disturbance in the form of undesired reflections in eyes and/or glasses originating from ambient light. Further preferably, the filter element has a passband matching a spectrum range in which the coherent light source has an energy emission peak. Thus, ideally, the filter element has a relatively narrow passband centered around the energy emission peak of the coherent light source. Alternatively, the filter element contains a low-pass filter configured to allow the energy emission peak and NIR (near infrared) light to pass through, however not visible light. In any case, the filter element may be arranged in front of, or behind a lens element; or be integrated into a lens element in the image registering means. Alternatively, the filter element may be included in a cover glass over the sensor element. Hence, by means of the filter element any interfering background light can be removed efficiently.

Preferably, a laser represents the coherent light source. Namely, a passively cooled laser typically has a bandwidth of less than 1 nm, whereas the LED (light emitting diode) light source used in the prior-art design normally has a bandwidth exceeding 40 nm. Thus, provided that a laser is used, it is comparatively straightforward to suppress any undesired background illumination.

According to another preferred embodiment of the invention, the light producing means also includes a second diffractive optical element. This element is configured to direct a light beam from the coherent light source towards a second designated area. The second designated area may here overlap the first designated area. Preferably, the second diffractive optical element is configured to produce a structured light, which when registered by the image registering means results in input data adapted for three-dimensional mapping. Thereby, so-called range mapping is facilitated, which in turn, facilitates the eye tracking.

According to still another preferred embodiment of the invention, the first diffractive optical element is configured to produce a homogeneous light pattern within the first designated area. As a result, a reliable eye tracking is further facilitated.

According to a further preferred embodiment of the invention, the apparatus includes control means configured to cause light from the coherent light source to pass through either a first or a second diffractive optical element in a time modulated manner, such that the first and second designated areas are illuminated during respective time intervals which are non-overlapping. Consequently, the image processing required for the eye tracking can be executed in an efficient manner.

Alternatively, or as a complement, the apparatus includes control means configured to cause light from the coherent light source to pass through a first and a second diffractive optical element in a wavelength multiplexed manner, such that coherent light with a first distinct wavelength is directed towards the first designated area, and coherent light with a second distinct wavelength is directed towards the second designated area. Again, this is beneficial for the required image processing.

According to another preferred embodiment of the invention, the apparatus includes at least two diffractive optical elements and a mirror element. The mirror element is here configured to be tilted in at least one dimension in response to a control signal. Depending on a degree of tilting, the mirror element directs collimated light from the coherent light source towards a given one of the at least two diffractive optical element. This offers a large degree of freedom in terms of where the collimated light is directed, as well as the shape/pattern of this light.

The proposed new design is generally advantageous in relation to the prior-art solutions because the new design is associated with higher conversion efficiency, has a more compact form factor, and enables illumination areas to be created which have arbitrary spatial shapes. For example collimation of the light beam from the proposed coherent light source renders it possible to evenly illuminate a designated area, such as a rectangle. This is beneficial both when using static and directable illuminators.

Moreover, a DOE has an efficiency of 90% for an analog design and more than 80% for a digital design. The form factor is drastically reduced by having a single laser diode instead of a matrix of incoherent light sources like LED elements. The DOE element size is the same as the beam size, typically around one millimeter. The optical elements of incoherent sources are typically in the order of 10 mm. Furthermore, laser diodes have a conversion efficiency of up to 70% whereas LED has a conversion efficiency of less than 30%.

The cost of one high power LED in an LED illuminator is in parity with that of one high power laser diode. In contrast to a typical LED illuminator, a laser diode system may be implemented based on a single chip. Moreover, high numerical aperture optics for LEDs is substantially bulkier than corresponding laser collimating optics. Therefore, a laser-based design may be manufactured at relatively low cost and small size.

Additionally, by using DOEs, large beam diameters and large diffuse apertures are enabled, which in turn, allow eye-safe operation. At the required powers, this is very difficult to attain with laser beams alone.

In contrast to LEDs, lasers have Gaussian beams, and multimode lasers have a supposition of Gaussian beams, which are well adapted for coupling into bulk optics or fiber optics. Due to lower diffraction, Gaussian beams may also be collimated and transmitted at larger distances than Lambertian sources.

By for example using collimated light it is relatively straightforward to control and couple bulk optics, or fibers, such that the illuminator acts as if it was positioned very close to the ideal position.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED
EMBODIMENTS OF THE INVENTION

The present invention concerns the tracking of a subject's eyes or gaze. Naturally, it is not excluded that, in addition thereto, the subject's facial features, facial expressions and/or gestures are tracked and/or analyzed. In this context, the invention solves the specific problem of directing light needed for achieving high enough image contrast towards the subject while minimizing the amount of superfluous light. The proposed apparatus may also provide homogenous illumination of a relatively large area covering the subject. In short, this is effected by shaping a light beam, such that an area towards which light is projected matches a field of view of an image sensor/camera used for registering image data representing relevant parts of the subject.

Of course, the illumination becomes even more energy-efficient if only the most relevant fraction of the camera's field of view is illuminated, e.g. where the subject's eyes are estimated to be located, and if the light beam is adaptively controlled to follow any movements of the subject. Below, we will describe various embodiments of the invention wherein such a control is attained.

Figure 1:
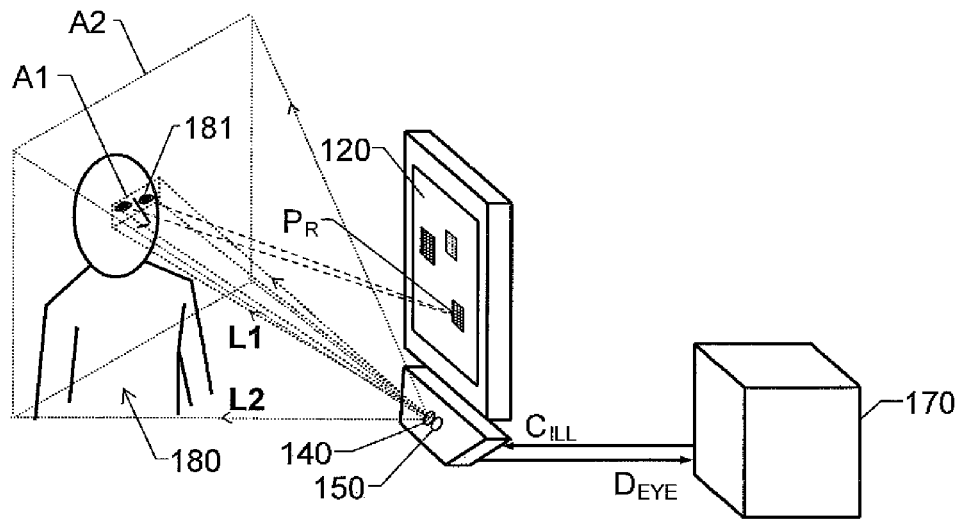
FIG. 1 shows an overview of an installation including an eye-tracker where a subject is illuminated by an apparatus according to the invention.

FIG. 1 shows an eye-tracking installation via which a user 180 may interact with a computer apparatus 170. As mentioned above, the invention is likewise applicable to eye/gaze-tracking where the resulting data $D_{EYE}$ does not produce any control signals, or the like.

In any event, a subject 180 is illuminated by an apparatus according to the invention. The proposed apparatus includes a light producing means 140 configured to provide at least one well-defined light beam L1 and L2, and image registering means 150.

The light producing means 140, in turn, includes a coherent light source configured to generate coherent light included in the at least one light beam L1 and L2. The light producing means 140 also contains a diffractive optical element, which is arranged between the coherent light source and an output from the light producing means 140. The characteristics of the diffractive optical element will be explained below with reference to FIGS. 2 to 8. However, in short, in response to a control signal $C_{ILL}$ (for example generated by the computer apparatus 170), the diffractive optical element is configured to direct light in the form of a first beam L1 towards a first designated area A1 that is estimated to cover the subject's 180 eyes.

The diffractive optical element may also be configured to direct light in the form of a second beam L2 towards a second designated area A2, for example including the first designated area A1. The second light beam L2 may contain so-called structured light having such properties that when light reflected from the second designated area A2 is registered by the image registering means 150, resulting data may be produced which is adapted for three-dimensional (3D) mapping. Thus, for example range mapping is facilitated. In contrast to what is illustrated in FIG. 1, however, this approach to 3D mapping requires off-axis illumination (i.e. an arrangement where the light producing means 140 is not co-located with the image registering means 150).

The image registering means 150 is configured to register light from the at least one light beam L1 and L2 having been reflected against the subject 180, for example in the first designated area A1. In response to the light registered by the image registering means 150, resulting data $D_{EYE}$ are produced, which resulting data $D_{EYE}$ represent movements of at least one eye of the subject 180.

The first designated area A1 may represent a particular illumination pattern, which renders a subsequent image processing for deriving the resulting data $D_{EYE}$ reliable and/or efficient. In any case, the first designated area A1 is located such that it appears within a field of view of the image registering means 150.

The subject 180 may be illuminated with light containing a combination of structured light for 3D mapping and homogeneous light for eye-tracking. A homogeneous light box is here preferably centered around a subject's eyes (i.e. the first designated area A1), whereas the structured light may be projected in a remaining field of view of the image registering means 150 (i.e. the second designated area A2).

According to embodiments of the invention, the second light beam L2 may contain homogenous light having a lower intensity than that of the first light beam L1. This type of light is advantageous, since it facilitates face identification and/or detection of facial features. Moreover, the homogenous light is useful if the eye-tracking has failed and needs to be restarted. In such a case, the initial eye-tracking is relatively coarse and requires a much larger illuminated area.

The coherent light source together with the diffractive optical element 145 causes very little stray light outside the first designated area A1. This facilitates a highly accurate control of the light delivery, especially compared to incoherent light sources.

Figure 2:
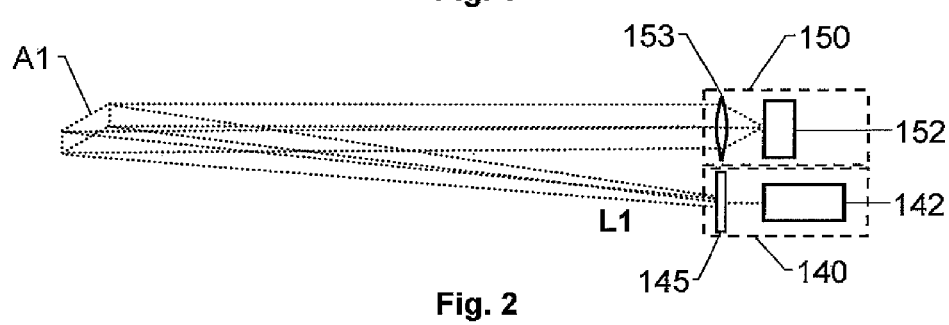
FIGS. 2-8 illustrates how one or more designated areas are illuminated and how image data representing those areas is recorded according to embodiments of the invention.

FIG. 2 illustrates how the first designated area A1 is illuminated, and how the image registering means 150 receives light reflected from that area A1 according to one embodiment of the invention.

The light producing means 140 contains a coherent light source 142, which is configured to generate coherent light to be projected towards the first designated area A1. A diffractive optical element 145 is arranged between the coherent light source 142 and an output from the light producing means 140. The diffractive optical element 145 is configured to direct the light beam L1 towards the first designated area A1, which in turn, is estimated to cover a body part of the subject 180 being relevant for the interface, i.e. typically at least one eye.

Analogous to what has been described above with reference to FIG. 1, the image registering means 150 registers light reflected from the first designated area A1, so that the resulting data $D_{EYE}$ can be produced. Of course, to this aim, the image registering means 150 contains at least one lens element 153 configured to project light towards a sensor element 152.

Figure 3:
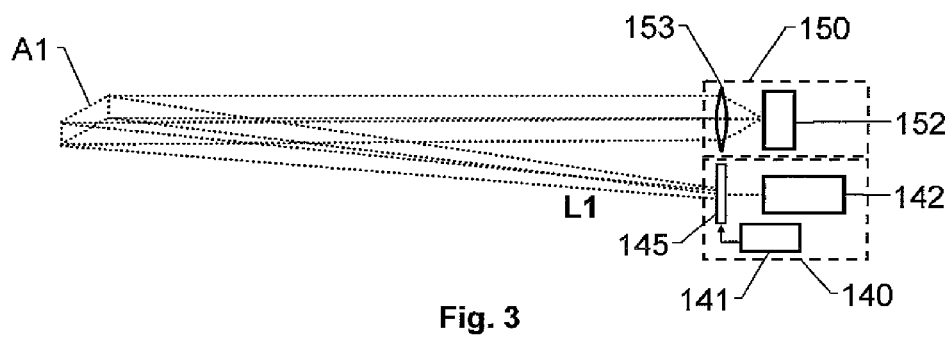

FIG. 3 illustrates how the first designated area A1 is illuminated and how the image registering means 150 receives light reflected from that area A1 according to another embodiment of the invention.

An undesired speckle pattern may occur in the first designated area A1. The speckle effect is a result of the interference of many light waves of the same frequency, having different phases and amplitudes, which add together to give a resultant wave whose amplitude, and therefore intensity, varies randomly.

To mitigate the speckle effect, the proposed apparatus may include a speckle reduction means. In FIG. 3, a speckle reduction means 141 is included, which contains an oscillator configured to cause the diffractive optical element 145 to move relative to the coherent light source 142. Thus, over time, the light from the beam L1 is distributed more even over the first designated area A1.

According to another embodiment of the invention (not shown), the coherent light source 142 instead includes a static multimode laser (transverse and/or longitudinal) configured to emit light with a spectrum containing at least two separate spectral lines. The light represented by each line is here associated with a particular and distinct speckle pattern. The resulting total light distribution over the first designated area A1 consequently becomes essentially even.

According to yet another embodiment of the invention (not shown), the speckle reduction means includes a modulating means configured to time-modulate the coherent light source 142 in such a manner that the coherent light source 142 produces light with a temporally varying speckle pattern. Again, over time, the resulting total light distribution over the first designated area A1 becomes essentially even.

Analogous to what has been described above with reference to FIG. 1, the image registering means 150 registers light reflected from the first designated area A1, so that the resulting data $D_{EYE}$ can be produced.

Figure 4:
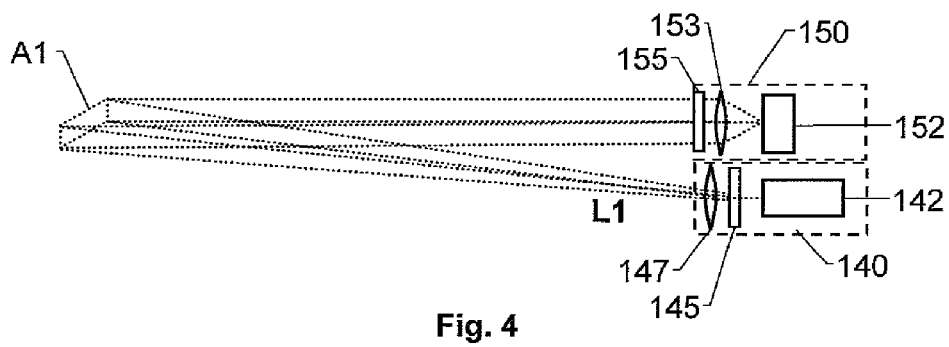

FIG. 4 illustrates how the first designated area A1 is illuminated and how image data representing that area A1 is recorded according to another embodiment of the invention. Here, a filter element 155 is arranged upstream of the sensor element 152 in the image registering means 150 configured to produce the resulting data $D_{EYE}$. The filter element 155 is configured to block visible light, so as to reduce disturbance caused by light sources in proximity to the apparatus, e.g. in the form of undesired reflections in eyes and/or glasses. It is further preferable if the filter element 155 is matched against an energy emission peak of the coherent light source 142. Ideally, this means that the filter element 155 has a relatively narrow passband centered around the energy emission peak of the coherent light source 142. Alternatively, however, the filter element 155 may include a low-pass filter allowing the energy emission peak and NIR (near infrared) light to pass through, however not visible light. Since a coherent light source 142 in the form of a passively cooled laser typically has a bandwidth of less than 1 nm the steepness requirements on the filter element 155 can be made rather moderate while suppressing the background illumination substantially.

In the embodiment shown in FIG. 4, a lens element 147 is included in the light path of the coherent light source 142 and the diffractive optical element 145. The lens element 147 may further shape and control the light towards the first designated area A1.

According to embodiments of the invention, the filter element 155 may either be arranged in front of the lens element 153 in the image registering means 150 (as shown in FIG. 4), or be arranged behind such a lens element. Alternatively, the filter element 155 may be integrated into the lens element, or be included in a cover glass over the sensor element 152.

Analogous to what has been described above with reference to FIG. 1, the image registering means 150 registers light reflected from the first designated area A1, so that the resulting data $D_{EYE}$ can be produced.

Figure 5:
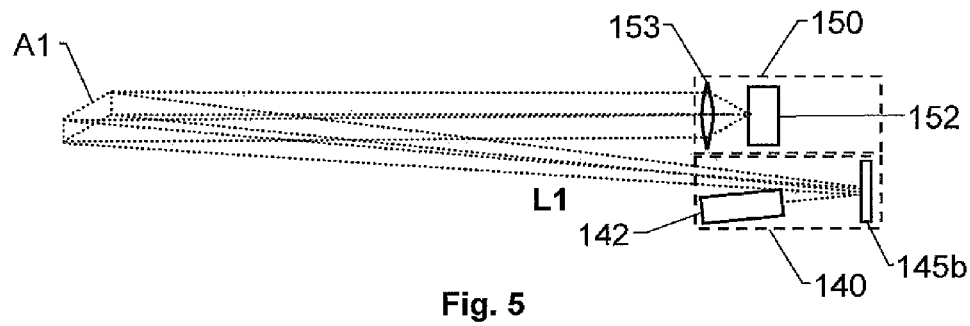

FIG. 5 illustrates how the first designated area A1 is illuminated and how image data are recorded according to yet another embodiment of the invention.

Here, the apparatus includes a light steering element 145b configured to receive the coherent light and direct at least a fraction thereof towards the subject 180. In addition to a diffractive optical element, the light steering element 145b may contain a mirror or a refractive device (e.g. a prism or a lens), configured to direct said fraction of the received light as a part of the first light beam L1 towards the first designated area A1. This provides a highly compact design.

Analogous to what has been described above with reference to FIG. 1, the image registering means 150 registers light reflected from the first designated area A1, so that the resulting data $D_{EYE}$ can be produced.

Figure 6:
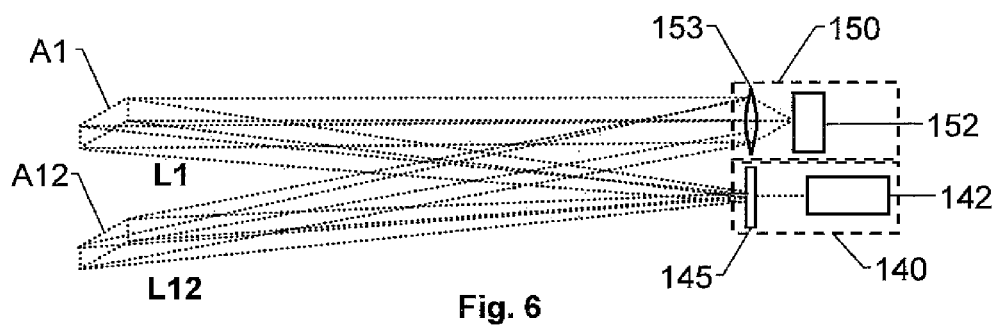

FIG. 6 illustrates how the first designated area A1 and a third designated area A12 are illuminated. Here, the diffractive optical element 145 is configured to direct a first light beam L1 from the coherent light source 142 towards the first designated area, and another light beam L12 from the coherent light source 142 towards a third designated area A12. Thus, the subject 180 may be illuminated at two separate and non-overlapping positions.

Analogous to what has been described above with reference to FIG. 1, the image registering means 150 registers light reflected from the first and third designated areas A1 and A12, so that the resulting data $D_{EYE}$ can be produced.

Figure 7:
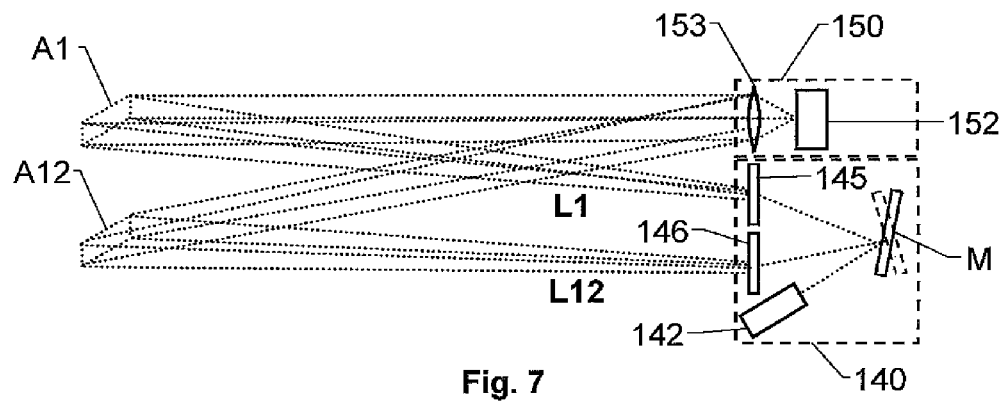

FIG. 7 illustrates, by another example, how the first designated area A1 and the third designated area A12 are illuminated.

In this embodiment, a common coherent light source 142 directs a first light beam L1 towards the first designated area, and another light beam L12 towards a third designated area A12, however via a first and a second diffractive optical element 145 and 146 respectively.

Control means (here represented by a mirror element M) are configured to cause light from the coherent light source 142 to pass through either the first or the second diffractive optical element 145 and 146 in a time modulated manner. As a result, the first and third designated areas. A1 and A12 are illuminated during respective time intervals which are non-overlapping.

The mirror element M is configured to be tilted in at least one dimension in response to a control signal, and depending on a degree of tilting, collimated light from the coherent light source 142 is directed towards a given one of the diffractive optical elements 145 and 146. Thus, the mirror element M and form factor can be minimized.

Alternatively, the apparatus may include control means (not shown), which are configured to cause light from the coherent light source 142 to pass through the first and second diffractive optical element 145 and 146 in a wavelength multiplexed manner, such that coherent light with a first distinct wavelength is directed towards the first designated area A1, and coherent light with a second distinct wavelength is directed towards the third designated area A12.

Furthermore, it is likewise possible that two or more diffractive optical elements are arranged in series with one another. For example a first diffractive optical element may be configured to spread the light from the coherent light source 142 to pass through two or more subsequent diffractive optical elements, which, in turn, each is configured to direct a fraction of the light to a designated area.

Analogous to what has been described above with reference to FIG. 1, the image registering means 150 registers light reflected from the first and third designated areas A1 and A12, so that the resulting data $D_{EYE}$ can be produced.

Figure 8:
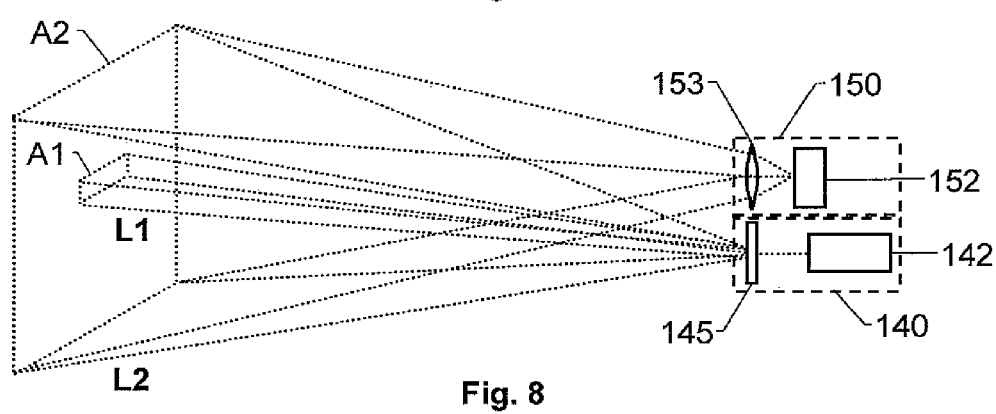

FIG. 8 illustrates how the first and second designated areas A1 and A2 may be illuminated. Essentially, the design is the same as that of FIG. 6 described above, but where the two illuminated areas overlap one another, Thus, the diffractive optical element 145 is configured to direct a first light beam L1 from the coherent light source 142 towards the first designated area, and a second light beam L2 from the coherent light source 142 towards the second designated area A12. Most preferably, however, the first and second designated areas A1 and A2 do not actually overlap one another. Although the position of the second area A2 is essentially static and the location of first area A1 is controlled to move inside the second area A2, the second area A2 is preferably generated with an "adaptive hole" corresponding to the first area A1 and its location. Namely, this is made possible through the proposed use of DOEs.

Analogous to what has been described above with reference to FIG. 1, the image registering means 150 registers light reflected from the first and third designated areas A1 and A12, so that the resulting data $D_{EYE}$ can be produced.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. An apparatus for illuminating a subject whose movements of at least one eye are to be registered by an eye-tracker to produce resulting data, the apparatus comprising:
   a light producing means configured to produce a light beam, and
   an image registering means configured to register light from the light beam having been reflected against the subject, the light producing means comprises:
   a coherent light source configured to generate coherent light included in the light beam, and
   a diffractive optical element arranged between the coherent light source and an output from the light producing means, the diffractive optical element being configured to direct a first light beam towards a first designated area covering at least said at least one eye of the subject, and direct a second light beam from the coherent light source towards a second designated area surrounding the first designated area.

2. The apparatus according to claim 1, wherein the first designated area represents an illumination pattern, and the first designated area is located within a field of view of the image registering means.

3. The apparatus according to claim 1, further comprising a speckle reduction means configured to reduce speckle-related intensity variations in the light from the coherent light source within the first designated area by causing the light from the coherent light source to be essentially evenly distributed over the first designated area during a predetermined interval of time.

4. The apparatus according to claim 3, wherein the speckle reduction means comprises an oscillator configured to cause the diffractive optical element to move relative to the coherent light source.

5. The apparatus according to claim 3, wherein the coherent light source comprises a static multimode laser configured to emit light with a spectrum containing at least two separate spectral lines, where the light represented by each of said at least two lines is associated with a particular speckle pattern.

6. The apparatus according to claim 3, wherein the speckle reduction means comprises a modulating means configured to time-modulate the coherent light source to produce light with a temporally varying speckle pattern.

7. The apparatus according to claim 1, further comprising a light steering element configured to receive the coherent light and direct at least a fraction of the received light towards the subject.

8. The apparatus according to claim 7, wherein the light steering element comprises a diffractive optical element configured to direct said fraction of the received light as a part of a first light beam towards the first designated area.

9. The apparatus according to claim 1, wherein the image registering means comprises a filter element arranged upstream of a sensor element configured to produce the resulting data, the filter element being configured to block visible light.

10. The apparatus according to claim 9, wherein the filter element has a passband matching a spectrum range in which the coherent light source has an energy emission peak.

11. The apparatus according to claim 1, wherein the light producing means comprises a second diffractive optical element configured to direct a second light beam from the coherent light source towards a second designated area.

12. The apparatus according to claim 11, wherein the second diffractive optical element is configured to produce a structured light which when registered by the image registering means creates resulting data EYE adapted for three-dimensional mapping.

13. The apparatus according to claim 11, further comprising control means configured to cause light from the coherent light source to pass through either the first or second diffractive optical element in a time modulated manner such that the first and second designated areas are illuminated during respective time intervals which are non-overlapping.

14. The apparatus according to claim 11, further comprising control means configured to cause light from the coherent light source to pass through the first and second diffractive optical element in a wavelength multiplexed manner such that coherent light with a first distinct wavelength is directed towards the first designated area, and coherent light with a second distinct wavelength is directed towards the second designated area.

15. The apparatus according to claim 1, wherein the first diffractive optical element is configured to produce a homogeneous light pattern within the first designated area.

16. The apparatus according to claim 15, wherein the apparatus is configured to adaptively control a location of the first designated area such that the first designated area covers at least an eye region of the subject at each point in time.

17. The apparatus according to claim 1, further comprising:
- at least two diffractive optical elements, and
- a mirror element configured to be tilted in at least one dimension in response to a control signal, and depending on a degree of tilting direct collimated light from the coherent light source towards a given one of the at least two diffractive optical element.

* * * * *